(12) United States Patent
Loh et al.

(10) Patent No.: US 7,767,788 B2
(45) Date of Patent: *Aug. 3, 2010

(54) FOLDING PROTEIN FUNCTIONING AS A MOLECULAR SWITCH

(75) Inventors: Stewart Loh, Manlius, NY (US); Mark C. Butler, Clearance, NY (US); Jeung-Hoi Ha, Manlius, NY (US); Tracy L. Radley, Liverpool, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/802,516

(22) Filed: Mar. 17, 2004

(65) Prior Publication Data

US 2004/0254774 A1    Dec. 16, 2004

Related U.S. Application Data

(60) Provisional application No. 60/456,965, filed on Mar. 21, 2003.

(51) Int. Cl.
*A61K 38/00* (2006.01)
*C07K 14/00* (2006.01)

(52) U.S. Cl. ............................... 530/350; 530/300
(58) Field of Classification Search ............... None
See application file for complete search history.

(56) References Cited

U.S. PATENT DOCUMENTS

| | | | |
|---|---|---|---|
| 4,977,248 | A | 12/1990 | Creighton |
| 5,265,030 | A | 11/1993 | Skolnick et al. |
| 5,436,850 | A | 7/1995 | Eisenberg et al. |
| 5,451,516 | A | 9/1995 | Matthews et al. |
| 5,600,571 | A | 2/1997 | Friesner et al. |
| 5,719,021 | A | 2/1998 | Inouye |
| 5,750,386 | A | 5/1998 | Conkling et al. |
| 5,792,625 | A | 8/1998 | Klaenhammer et al. |
| 5,866,119 | A | 2/1999 | Bandman et al. |
| 5,935,934 | A | 8/1999 | Vegeto et al. |
| 5,955,073 | A | 9/1999 | Rybak et al. |
| 5,965,396 | A | 10/1999 | Pan et al. |
| 5,972,678 | A | 10/1999 | Silverman et al. |
| 6,045,793 | A | 4/2000 | Rybak et al. |
| 6,107,094 | A | 8/2000 | Crooke |
| 6,136,576 | A | 10/2000 | Diaz-Torres et al. |
| 6,178,384 | B1 | 1/2001 | Kolossv et al. |
| 6,214,982 | B1 | 4/2001 | Pasloske et al. |
| 6,280,991 | B1 | 8/2001 | Raines |
| 6,294,353 | B1 * | 9/2001 | Pack et al. .................. 435/69.1 |
| 6,476,194 | B1 | 11/2002 | Tessier et al. |
| 6,511,829 | B1 | 1/2003 | Ernst |
| 6,528,276 | B1 | 3/2003 | Germann et al. |

OTHER PUBLICATIONS

Scalley-Kim et al. (Protein Sci., Feb. 2003; 12: 197-206).*
Minard et al. (Protein Sci., 2001; 10, p. 129-134).*
Olivia et al. (J. Mol. Biol., 1997, 266, p. 814-830).*
Doi et al., FEBS Letters, 1999, vol. 457, p. 1-4.*
Hochstrasser (Nature Cell Biology, 2000, vol. 2, p. E153-E157).*
Sevcik et al., J. Biol. Chem., Dec. 6, 2002, vol. 277, Issue 49, p. 47325-47330.*
Wintrode et al., Proteins: Structure, Function, and Genetics, 1994, p. 18246-18253.*
Pace et al., Biochemistry, 1992, vol. 31, p. 2728-2734.*
Varshaysky, Proc. Natl. Acad. Sci., Mar. 1998, vol. 95, pp. 2094-2099.*
Pedersen et al., J. Mol. Biol., 2002, vol. 323, p. 115-123.*
NCBI, Conserved Domain Search, www.ncbi.nlm.nih.gov/structure/cdd/wrpsb.cgi, "barnase", p. 1.*
NCBI, Conserved Domain Search, www.ncbi.nlm.nih.gov/structure/cdd/wrpsb.cgi, "ubiquitin", p. 1.*

* cited by examiner

*Primary Examiner*—Shubo (Joe) Zhou
*Assistant Examiner*—Pablo Whaley
(74) *Attorney, Agent, or Firm*—Ryan, Mason & Lewis, LLP

(57) ABSTRACT

The present invention is a two-domain, bi-functional fusion protein that functions as a molecular switch wherein the free energy released by the folding of a first domain of the fusion protein drives an unfolding of a second domain of the fusion protein, and vice versa. The molecular structure of the fusion protein is engineered so that, at any time, the folding of the first domain necessarily unfolds the other domain, and vice versa, thereby making the folded and unfolded states of the first and second domains mutually exclusive. This is accomplished by the insertion of ubiquitin insert protein into a surface loop of barnase target protein subject to the structural design criterion that the N-C terminal length of the ubiquitin insert protein is at least two-times greater than the Cα-Cα alpha-carbon-alpha-carbon length of the surface loop of the barnase target protein.

**7 Cla

FOLDING PROTEIN FUNCTIONING AS A MOLECULAR SWITCH

RELATED APPLICATIONS

The present invention claims priority to U.S. Provisional No. 60/456,965 filed on Mar. 21, 2003, which is incorporated by reference in its entirety.

STATEMENT REGARDING FEDERALLY SPONSORED RESEARCH & DEVELOPMENT

Some of the research described in this application was funded by a grant (5R01GM5700904) from the National Institutes of Health and a grant from the Department of Defense (DAMD179818558). The U.S. government may therefore have certain rights in the invention.

BACKGROUND OF THE INVENTION

The invention relates generally to a fusion protein.

1. Technical Field
2. Related Art

Ribonucleases are hydrolase enzymes that break linkages between nucleotides in ribonucleic acid. They are accordingly highly cytotoxic. A major problem with their use as therapeutic agents, for example, as pharmacologic agents in the treatment of cancer, is that their cytotoxicity is indiscriminate. Currently available ribonuclease pharmacologic agents kill normal as well as neoplastic cells, and the side effects of their use can be severe. Additionally, currently available ribonuclease agents demonstrate poor bioavailability owing to their rapid degradation by the liver and their difficulty in passing through both normal and neoplastic cell membranes.

SUMMARY OF THE INVENTION

The present invention comprises a fusion protein (and a method for the creation thereof), which fusion protein includes a ubiquitin insert protein having an insert regulatory domain lying between an amino terminal and a carboxyl terminal of the ubiquitin insert protein, the ubiquitin insert protein being associated with a first quantity of free energy; and, a barnase target protein having a surface loop that begins at an alpha carbon of an initial amino acid of the surface loop and terminates at an alpha carbon of a terminal amino acid of the surface loop, the surface loop comprising a target cytotoxic domain of the barnase target protein, the target cytotoxic domain being associated with a second quantity of free energy, wherein, the ubiquitin insert protein is inserted at a point within the surface loop between the alpha carbon of the first amino acid of the surface loop and the alpha carbon of the terminal amino acid of the surface loop, such that an amino-carboxyl length of the ubiquitin insert protein is at least two-times greater than an alpha carbon-alpha carbon length of the barnase target protein.

DETAILED DESCRIPTION OF THE INVENTION

Figure 1A:
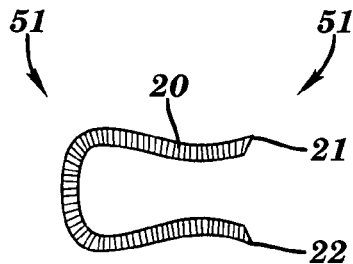
FIG. 1A is a schematic illustration of an insert regulatory domain of a ubiquitin insert protein in an unfolded conformation.

The fusion protein of the present invention functions as a mutually exclusive folding domain molecular switch, possessing the following advantages:

a) the mechanism of the fusion protein is inherently cooperative; and, b) the all-or-nothing action of the switching mechanism of the fusion protein assures that the fusion protein behaves in a binary fusion; and, c) the switching mechanism of the fusion protein is reversible; and, d) the position of a reciprocally folding and unfolding conformational equilibrium of the fusion protein, to be described hereinafter, can be readily adjusted by external factors.

In their simplest form, proteins are polypeptides, i.e., linear polymers of amino acid monomers. However, the polymerization reaction which produces a polypeptide results in the loss of one molecule of water from each amino acid. Consequently, a polypeptide is more rigorously defined as a polymer of amino acid residues. Natural protein molecules may contain as many as 20 different types of amino acid residues, each of which contains a distinctive side chain.

An amino acid is an organic molecule containing an amino group ("—$NH_2$") and a carboxylic acid group ("—COOH"). While there are many forms of amino acids, all of the important amino acids found in living organisms are alpha-amino acids. Alpha amino acids have their both their —COOH and —NH$_2$ groups attached to the same carbon atom, which is called the alpha carbon atom.

Thus, all of the important amino acids found in living organisms consist of an alpha carbon atom to which there is attached:
- a) A hydrogen atom;
- b) An amino group (—NH$_2$);
- c) a carboxyl group (—COOH);
- d) One of 20 different "R" groups.

It is the structure of the R group that distinguishes each amino acid structurally and determines its biochemical properties. Moreover, the structure and biochemical properties of a protein are dictated by the precise sequence of the amino acids in the polypeptide chains of which it is comprised. One end of every polypeptide, called the amino terminal or N-terminal, has a free amino group (—NH2). The other end, has a free carboxyl group (—COOH), and is called the carboxyl terminal or C-terminal.

The particular linear sequence of amino acid residues in the polypeptide chain comprising a protein defines the primary structure of that protein. However individual polypeptides and groups of polypeptides undergo spontaneous structural alteration and association into a number of recurring intermediate patterns such as, for example, helices, including alpha helices, and sheets, including beta sheets. These recurring intermediate polypeptide patterns are referred to as a protein's secondary structure. The spontaneous structural alteration and association of polypeptide chains into a secondary structure is determined by the sequence of amino acids in the polypeptide chains and by the ambient biochemical environment.

The helices, sheets, and other patterns of a protein's secondary structure additionally undergo a process of thermodynamically-preferred compound folding to produce a three-dimensional or tertiary structure of the protein. The fully folded conformation of the protein is maintained by relatively weak inter-atomic forces such as, for example, hydrogen bonding, hydrophobic interactions and charge-charge interactions. Covalent bonds between sulphur atoms may also participate in protein folding into a tertiary conformation by forming intra-molecular disulfide bridges in a single polypeptide chain, as well as by forming intermolecular disulfide bridges between separate polypeptide chains of a protein. This ability of polypeptide chains to fold into a great variety of structures, combined with the large number of amino acid sequences of a polypeptide chain that can be derived from the 20 common amino acids in proteins, confers on protein molecules their great range of biological activity.

The tertiary structure of a protein may contain a surface loop. A surface loop is continuous length of polypeptide chain whose constituent amino acids are in neither an alpha helical conformation nor in a beta sheet conformation, and can contact at least five water molecules, as determined by the DSSP computer program of Wolfgang Kabasch and Chris Sander. The DSSP, a program which is well known in the art, defines a secondary structure, geometrical features and solvent exposure of proteins, given atomic coordinates in Protein Data Bank format, which is also well known in the art. (W. Kabasch & C. Sander, "Dictionary of protein secondary structure: pattern recognition of hydrogen-bonded and geometrical figures", Biopolymers 22, 2577-2637.

Consistently with the foregoing definition, the term "surface loop" additionally means the target cytotoxic domain of the barnase target protein, beginning at an alpha carbon of an initial amino acid of the surface loop and terminating at an alpha carbon of a terminal amino acid of the surface loop.

Protein folding occurs on a global level that endows the entire protein molecule with a three dimensional structure and surface topology. Protein folding also occurs at a local level at multiple sites upon and within a protein. Locally, folding may involve one or more polypeptide subunits of the protein to endow different regions of the protein with different specific biological activities, or different specific molecular architectures, such as, for example, fashioning a location in a protein molecule into a receptor site for another molecule.

As used herein, the term domain means the molecular structure of an entire protein molecule or the molecular structure of a part, portion, or region of the molecular structure of a protein molecule, including a part, portion, or region of the protein molecule's surface or the protein molecule's interior. A domain may refer only to a distinction in a protein molecule's structure, such as for example, an alpha helix or a beta sheet. A domain may or may not have an associated biological function, such as a regulatory, receptor, signaling, active, catalytic, or other biological function. A domain may further be associated with a free energy, i.e., a thermodynamic state function that indicates the amount of energy that stabilizes the domain when the protein, or part thereof, with which the domain is associated is in a folded configuration. All of part of the free energy may be available for the domain to do biochemical work.

Because the folding of a protein molecule is both a global and local process, it can endow a protein molecule with both global and local structural and biological properties, such as, for example, an enzymatic activity, or a capacity and specifying for binding other proteins, such as antigens. Consequently, the biological functions of a protein depend on both its global folded tertiary structure, which is also called its native or folded conformation, as well as the folded structure of regions of the protein. Conversely, a global or local unfolding of a protein deactivates its global or local biological activity. An unfolded, biologically inactive protein is said to be in a denatured or unfolded conformation.

Many proteins are comprised of domains that communicate with each other by means of conformational changes in the structure of the protein of which they are a part, in order to activate or deactivate a biological function. For example, in the case of a protein that is an enzyme, ligand binding or phosphorylation can serve as a switching mechanism to induce structural changes within the enzyme's regulatory domain, which then triggers activity in the enzyme's catalytic domain.

Another type of switching mechanisms is illustrated in vivo by proteins that are unfolded in physiological conditions but fold upon binding to a cellular target. In this molecular switching mechanism, the folding and unfolding of a regulatory domain of a protein modulates the function of the protein via propagation of structural changes to its active domain.

The fusion protein herein is synthesized from:

a) a ubiquitin insert protein having an insert regulatory domain lying between an amino terminal and a carboxyl terminal of the ubiquitin insert protein, which insert regulatory domain is associated with a first quantity of free energy; and, b) a barnase target protein having a surface loop that begins at an alpha carbon of an initial amino acid of the surface loop and terminates at an alpha carbon of a terminal amino acid of the surface loop, which surface loop comprises a target cytotoxic domain associated with a second quantity of free energy.

The amino terminal of the ubiquitin insert protein is spatially separated from the carboxyl terminal of the ubiquitin insert protein by a linear (i.e., straight line) distance known as the amino-carboxyl length (hereinafter, the "N-C terminal length") of the ubiquitin insert protein, that is measured when the ubiquitin insert protein is in its folded conformation; see, e.g. double-headed arrow in FIG. 2A. The alpha carbon of the initial amino acid of the surface loop of the barnase target protein is spatially separated from the alpha carbon of the terminal amino acid of the surface loop of the barnase target protein by a linear (i.e., straight line) distance known as the alpha-carbon-alpha-carbon length of the surface loop of the barnase target protein (hereinafter, the "Calpha-Calpha length"), that is measured when the barnase target protein is in its folded conformation; see, e.g. double-headed arrow in FIG. 2B.

The molecular structure of the ubiquitin-barnase fusion protein is engineered so that, at any time, the folding of the ubiquitin insert regulatory domain necessarily unfolds the barnase target cytotoxic domain, and vice versa, thereby making the folded and unfolded states of the insert regulatory and target cytotoxic domain mutually exclusive. This mutual exclusion of concurrently folded or concurrently unfolded states is accomplished by the insertion of the ubiquitin insert protein into the surface loop of the barnase target protein subject to a novel structural design criterion wherein the N-C terminal length of the ubiquitin insert protein is at least two-times greater than the Calpha-Calpha length of the surface loop of the barnase target protein.

The present invention is thus a fusion protein that functions as a molecular switch wherein the free energy released by the folding of the ubiquitin insert regulatory domain of the fusion protein drives the unfolding of the barnase target cytotoxic domain of the fusion protein, and vice versa.

Subject to this novel structural design criterion, a dynamic state of thermodynamic and structural equilibrium is established in the fusion protein that disenables the regulatory insert domain of the ubiquitin insert protein and the cytotoxic target domain of the barnase target protein from simultaneously co-existing in their native folded states.

Accordingly, any excess free energy present in one of the two domains that is not necessary to stabilize its folded configuration is spontaneously transferred, through the structure of the fusion protein, to the other of the two domains to unfold it from its folded configuration, and vice versa. In effect, the excess free energy stored in the folded conformation of one domain is used to drive the unfolding of the other domain; and, the molecular structure of the fusion protein is engineered to create a dynamic state of thermodynamic and correlative structural equilibrium that is determined by the relative thermodynamic and structural stabilities of the two domains.

Viewed another way, the molecular structure of the fusion protein is engineered to create a molecular switch by creating cooperatively folding-unfolding subunits comprising two protein domains, which two domains cannot simultaneously exist in their folded states. This scheme is depicted in FIGS. 1A-F.

FIG. 1A is a schematic illustration of an insert regulatory domain of a ubiquitin insert protein in an unfolded conformations. In FIG. 1A, ubiquitin insert protein 51, having an amino terminal 21 and a carboxyl terminal 22, exists in an unfolded conformation 20, thereby forming an unfolded insert regulatory domain, schematically illustrated as a hatched ribbon that is coincident with the extent of ubiquitin insert protein 51.

Figure 1B:
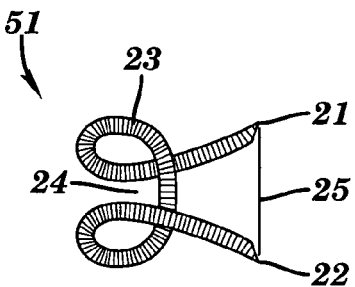
FIG. 1B is a schematic illustration of an insert regulatory domain of a ubiquitin insert protein in an folded conformation.

FIG. 1B is a schematic illustration of an insert regulatory domain of a ubiquitin insert protein in an folded conformation. In FIG. 1B, ubiquitin insert protein 51, having an amino terminal 21 and a carboxyl terminal 22, exists in a folded conformation 23, thereby forming a folded insert regulatory domain, schematically illustrated as a hatched double-cross ribbon that is coincident with the extent of ubiquitin insert protein 51, and folds to form indentation 24.

Figure 2A:
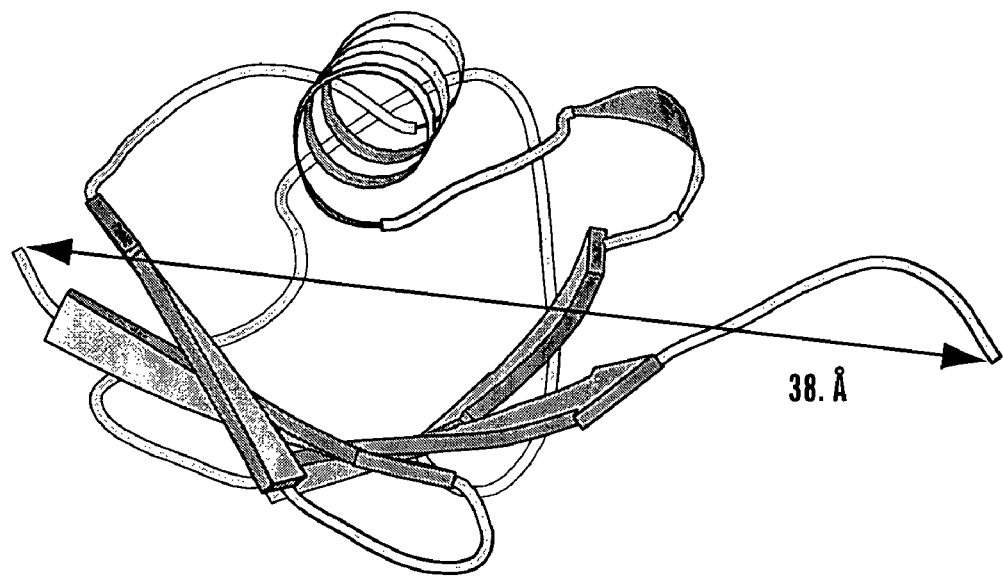
FIG. 2A is a schematic illustration of a human ubiquitin molecule.

In FIG. 1B, reference numeral 25 refers to the amino-carboxyl length of insert regulatory domain of insert protein barnase in its folded conformation (corresponding to double-headed arrow labeled 38 Å in FIG. 2A). The amino-carboxyl length of the insert regulatory domain of insert protein barnase in its folded conformation is synonymous with the N-C terminal length of the labeled 38 Å in FIG. 2A). The amino-carboxyl length of the insert regulatory domain of insert protein barnase in its folded conformation (also corresponding to double-headed arrow labeled 38 Å in FIG. 2A).

Figure 1C:
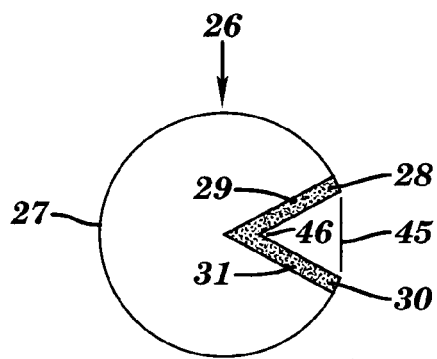
FIG. 1C is a schematic illustration of a conformation of a barnase target protein having a folded target cytotoxic domain in the shape of a wedge and having a surface loop.

In FIG. 1C, there is shown schematically a folded conformation 26 of a barnase target protein 41 having a folded target cytotoxic domain in the shape of a wedge 46. Barnase target protein 41 also has a surface loop 27, schematically shown as a nearly full circle, arising from an alpha carbon of an initial amino acid of the surface loop, forming a beginning 28 (of a first arm 29) of wedge 46, and ending at an alpha carbon of a terminal amino acid of the surface loop, forming an end 30 (of a second arm 31) of wedge 46.

Also shown schematically in FIG. 1C is line 45, representing the (straight) Caplha-Calpha length of the surface loop 27.

Figure 1D:
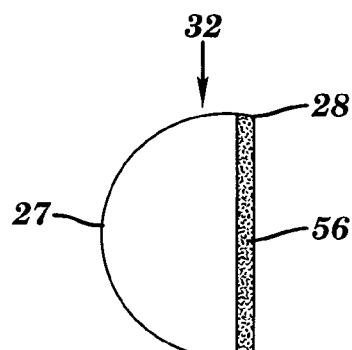
FIG. 1D is a schematic illustration of a conformation of a barnase target protein having an unfolded target cytotoxic domain in the shape of a straight line and having a surface loop.

In FIG. 1D, there is shown schematically an unfolded conformation 32 of barnase target protein 41 in which folded target cytotoxic domain 46 (of FIG. 1C) has unfolded into the shape of straight line 56. Unfolded conformations 32 of barnase target protein 41 also has surface loop 27, now shown as a half-circle arising from the alpha carbon forming the beginning 28 of the straight line 56 and ending at the alpha carbon forming the end 30 of the straight line 56.

Figure 1E:
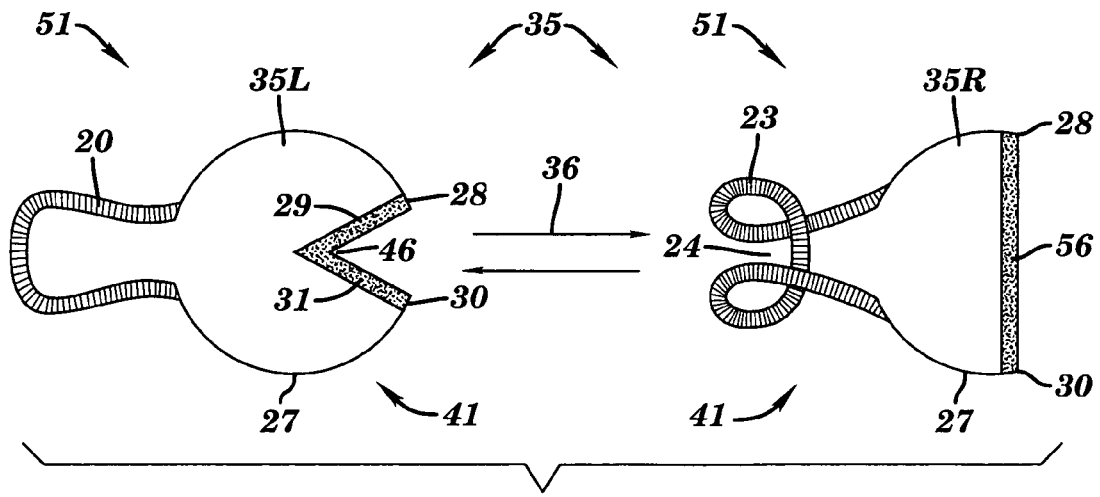
FIG. 1E is a schematic illustration of a ubiquitin-barnase fusion protein capable of existing in two mutually exclusive conformations.

In FIG. 1E, there is shown schematically a ubiquitin-barnase fusion protein 35 including ubiquitin insert protein 51 inserted into surface loop 27 of barnase target protein 41, which ubiquitin-barnase fusion protein 35 is capable of existing in two mutually exclusive conformations 35L and 35R, representing the mutually exclusive binary states of the ubiquitin-barnase fusion protein 35.

The image to the left of the antiparallel arrows 36 of FIG. 1E shows exclusive state 35L of ubiquitin-barnase fusion protein 35, wherein ubiquitin insert protein 51, with its insert regulatory domain in unfolded (hatched ribbon) conformation 20, (as shown in FIG. 1A), has been inserted into surface loop 27 of barnase target protein 41 with its target cytotoxic domain in its folded conformation 46, (as shown in FIG. 1C). The image to the right of the antiparallel arrows 36 of FIG. 1E shows exclusive state 35R of ubiquitin-barnase fusion protein 35, wherein ubiquitin insert protein 51, with its insert regulatory domain in its folded (hatched double-cross ribbon) conformations 23, (as shown in FIG. 1B), inserted into surface loop 27 of barnase target protein 41 with its target cytotoxic domain in its unfolded (straight lines) conformation 56 (as shown in FIG. 1D).

Figure 1F:
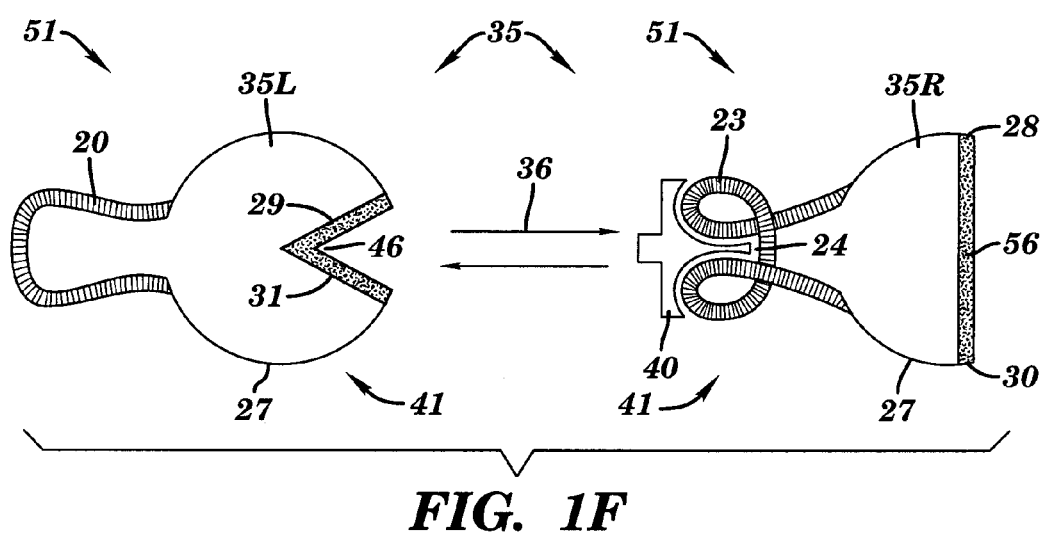
FIG. 1F is a schematic illustration of a ubiquitin-barnase fusion protein capable of existing in two mutually exclusive conformations, in which an equilibrium state has been influenced by the binding of a ligand.

In FIG. 1F, fusion protein 35 is again shown schematically existing in two mutually exclusive conformations 35L and 35R, representing the mutually exclusive binary states of fusion protein 35. However, the dynamic equilibrium existing between conformations 35L and 35R has been shifted to the right by binding the exemplary ligand 40 to the indentation 24 of insert regulatory domain of protein 51 in folded conformation 23.

If insert regulatory domain of ubiquitin insert protein 51 in folded conformation 23 (FIG. 1B and FIG. 1E Right) is more stable than target cytotoxic domain of barnase target protein 41 in its folded conformation 26, (FIG. 1C and FIG. 1E Left), then insert regulatory domain of ubiquitin insert protein 51 in folded conformation 23 (FIG. 1B and FIG. 1E Right) will have an excess of free energy with which to forcibly stretch and unfold folded conformation 26 of target cytotoxic domain of barnase target protein 41 (FIG. 1C and FIG. 1E Left), thereby unfolding wedge 46 into line 56, and yielding ubiquitin-barnase fusion protein 35 in state 35R.

If target cytotoxic domain of barnase target protein 41 in folded conformation 26 (FIG. 1C and FIG. 1E Left) is more stable than insert regulatory domain of ubiquitin insert protein 51 in folded conformation 23 (FIG. 1B and FIG. 1E Right), then target cytotoxic domain of barnase target protein 41 in its folded conformation 26 (FIG. 1C and FIG. 1E Left) will have an excess of free energy with which to forcibly stretch and unfold insert regulatory domain of ubiquitin insert protein 51 in folded conformation 23 (FIG. 1B and FIG. 1E Right), thereby folding line 56 into wedge 46, and yielding ubiquitin-barnase fusion protein 35 in state 35L.

In this manner, the ubiquitin-barnase fusion protein fully exploits the free energy stored in the folded conformations of the aforementioned domains, as well as the inherent cooperatively of reciprocal domain folding, to create a molecular switch of unprecedented efficiency.

The ubiquitin-barnase fusion protein is a novel and powerful approach to understanding the fundamental mechanisms of allosteric switching in molecular biology and for the developing diagnostic and therapeutic proteins with novel capabilities, possessing the following advantages:

a) the mechanism of the molecular switch it is inherently cooperative; and, b) the all-or-nothing action of the mechanism of the molecular switch assures that it behaves in a binary fusion; and, c) the switching mechanism is reversible; and, d) the position of the folding/unfolding equilibrium can be readily adjusted by external factors.

For example, When present at 1 mM concentration, a ligand that binds to a protein with a dissociation constant of 1 nM, will stabilize the native conformation of the protein by as much as RT ° ln($10^3$), or 4.2 kcal mol$^{-1}$ at 37 degrees C. This value is comparable to the total free energy change of folding for many proteins.

As indicated, barnase is a highly cytotoxic ribonuclease that breaks linkages between nucleotides in ribonucleic acid. A major problem with its use as a pharmacologic agent, e.g., in the treatment of cancer, is that its cytotoxicity is indiscriminate. Currently available ribonuclease pharmacologic agents, such as barnase, kill normal as well as neoplastic cells, and the side effects of their use can be severe.

Because, the regulatory domain of ubiquitin and the cytotoxic domain of barnase cannot simultaneously co-exist in their folded states, the regulatory domain of ubiquitin, may be used to regulate the cytotoxic activity of barnase. Moreover, the ubiquitin and barnase domains participate in a cooperative and reversible conformational equilibrium that may be influenced and controlled by a variety of controllable effector signals such as, for example, ligand binding, pH, temperature, chemical denaturants, or the presence of stabilizing or destabilizing mutations in either the barnase or ubiquitin domains.

The two-domain, bi-functional ubiquitin-barnase fusion protein is not limited to the insertion of a ubiquitin insert protein into a barnase target protein having only one domain or only one biological function. The two-domain, bi-functional ubiquitin-barnase fusion protein_disclosed herein comprises cases wherein one or more exemplary insert proteins is inserted into one or more surface loops of exemplary target proteins having multiple domains and multiple biological functions, the effect of these insertions being to form a one or more cooperatively folding-unfolding subunits in the resultant fusion protein, each comprising two protein domains, which two domains cannot simultaneously exist in their folded states, thereby forming one or more cooperative, reversible, molecular switches in the same fusion protein, each of which is responsive to different controllable effector signals such as, for example, ligand binding, pH, temperature, chemical denaturants, or the presence of stabilizing or destabilizing mutations in the domains.

To create the two-domain bifunctional ubiquitin-barnase fusion protein, the inventors herein inserted the human ubiquitin molecule having one regulatory domain, into a selected surface loop of the barnase target protein, which surface loop has one catalytic (or cytotoxic) domain.

The exemplary insert protein, human ubiquitin, is a protein having one regulatory domain, and one biological function, that of serving as a signaling marker or flag.

The exemplary target protein, barnase is a ribonucelase produced exclusively by the bacterium *Bacillus amyloliquefaciens*. Barnase has one catalytic domain that is functionally cytotoxic to all mammalian cell types.

FIG. 2A is a schematic illustration a molecule of human ubiquitin. The sheet-like arrows and ribbons in FIG. 2A represent beta strands and alpha helices, respectively. The noodle-like strands in the protein are loops and turns of the ubiquitin molecule. In FIG. 2A, the N-C terminal length from ubiquitin is about 38 Å in its folded conformation, as indicated by the double-headed straight-line arrows bearing the bearing the legend "38 Å", a magnitude that measures the straight-line distance between an N-terminal amino acid at which one arrowhead begins and a C-terminal amino acid, at which the opposing arrow head ends.

Figure 2B:
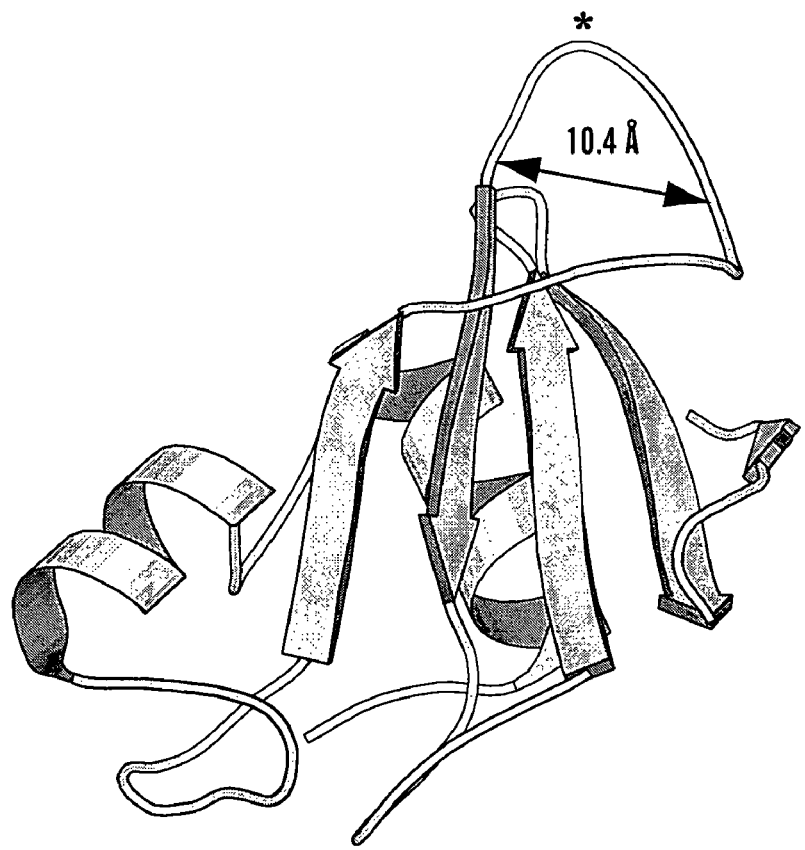
FIG. 2B is a schematic illustration of a barnase molecule.

FIG. 2B is a schematic illustration a barnase molecular. The sheet-like arrows and ribbons in FIG. 2A represent beta strands and alpha helices, respectively. The noodle-like strands in the protein are loops and turns of the barnase molecule. The barnase molecule has a surface loop in which the Calpha-Calpha length, measured from alpha-carbon of the loop amino acid proline in the number 64 positions ("Pro64") to the alpha-carbon of the loop amino acid threonine in the number 70 position ("Thr70") is about 10.4 Å, with the barnase molecule in its folded conformation, as indicated by the double-headed straight-line arrow bearing the legend "10.4 Å", a magnitude that measures the straight-line distance between an alpha carbon at which one arrowhead begins, and another alpha carbon, at which the opposing arrow head ends. The asterisk in FIG. 2B represents the point at which the ubiquitin molecule, shown in FIG. 2A is inserted between amino acid residue 66 and amino acid residue 67 of barnase.

The exemplary insert protein ubiquitin and the exemplary target protein barnase satisfy the novel structural design criterion that the straight line N-C terminal length of the exemplary insert protein be at least twice the straight line Calpha-Calpha length of the exemplary target protein surface loop selected for insertion. In the exemplary fusion protein resulting from the insertion of the exemplary insert protein ubiquitin molecule into the surface loop of the exemplary target protein barnase, the foregoing structural design criterion is satisfied.

Consequently, the regulatory domain of ubiquitin and the catalytic domain of barnase cannot simultaneously co-exist in their folded states; and, the regulatory domain of ubiquitin, may be used to regulate the cytotoxic activity of barnase. Moreover, the ubiquitin and barnase domains participate in a cooperative and reversible conformational equilibrium, that may be influenced an controlled by a variety of controllable effector signals such as, for example, ligand binding, pH, temperature, chemical denaturants, or the presence of stabilizing or destabilizing mutations in either the barnase or ubiquitin domains.

The ubiquitin and barnase genes are created by annealing and ligating synthetic oligonculeotides (Integrated DNA Technologies) according to standard protocols.

The ubiquitin-barnase fusion gene is made by first adding an exemplary five amino acid linker (Gly-Thr-Gly-Gly-Ser) between the Lys66 and Ser67 codons of the barnase gene. The inserted DNA contains exemplary KpnI and BamHI restriction sites that are used to introduce the ubiquitin gene.

The exemplary five amino acids of the exemplary linker individually serve as short, flexible linkers at the points of attachment. The ubiquitin gene is inserted between the Thr and Gly codons of the linker.

All genes are fully sequenced to verify their integrity.

An interim ubiquitin-barnase fusion expression plasmid pETMT is created by using exemplary NdeI and XhoI enzymes to insert the ubiquitin-barnase fusion gene into a plasmid, such as, for example, a pET256(+) plasmid (Novagen), or any other T7 promoter-containing plasmid that also confers resistance to an antibiotic other than ampicillin.

In order to make the plasmid stable in *E. coli,* the gene for barstar, the intracellular inhibitor of barnase that is co-expressed with barnase by *Bacillus amyloliquefaciens* (together with its natural promoter from *Bacillus amuloliquefaciens*), is cleaved out of an exemplary pMT1002 plasmid (gift of Dr. Y. Bai, National Institutes of Health), or any other T7 promoter-containing plasmid that also confers resistance to an antibiotic other than ampicillin, with ClaI and PstI enzymes. The barstar gene is then placed between ClaI and PstI restriction sites on the pETMT plasmid (prior to this step, these sites are introduced using the QuickChange mutagenesis kit (Strategene)).

In order to obtain milligram quantities of the ubiquitin-barnase fusion protein, it is necessary to increase cellular levels of barstar and purify the inactive ubiquitin-barnase fusion-barstar complex. Accordingly, the barstar gene is cloned into an exemplary pET41 plasmid (Novagen), thereby placing it under control of a T7 promoter and conferring upon the transformed cells resistance to kanamycin or any other antibiotic other than ampicillin.

*E. coli* BL21 (DE3) cells are transformed with both plasmids, grown in a temperature range between about 20 degrees C. and 37 degrees C. in exemplary Luria-Bertani medium containing ampicillin and kanamycin to OD600=1.0, and induced with 100 mg/L IPTG. Bacteria are harvested about 2 to 12 hours later by centrifugation.

Cells are lysed in about 10 mM sodium phosphate (pH 7.5) by repeated freeze-thaw cycles in the presence of a small amount of lysozyme at a concentration of about lysozyme is 10 mg/liter. Exemplary DNase I (Sigma) at a concentration of about 10 mg/liter is then added to reduce viscosity, and the solution is centrifuged to remove insolubles. 8 M urea is added to the supernatant to dissociate bound barstar, which is subsequently removed by passing the solution through DE52 resin (Whatman) or a substantially equivalent anion exchange chromatography resin. The solution is then loaded onto a HiTrap heparin column (Amersham-Pharmacia) or substantially equivalent cation exchange column, washed with 10 mM sodium phosphate (pH 7.5) and 6 M urea, and eluted with a 0-0.2 M NaCl gradient.

Western blot analysis using anti-ubiquitin antibodies is used to show that the major impurities are truncated ubiquitin-barnase protein products in which the ubiquitin domain, which is unfolded in the ubiquitin-barnase fusion protein-barstar complex, is partially digested. These proteins, however, elute significantly later than the intact ubiquitin-barnase fusion protein in the NaCl gradient. The urea is removed by dialysis against double-distilled water, to yield barnase-ubiquitin fusion protein that is approximately 95% pure as judged by sodium dodecyl sulfate polyacrylamide gel electrophoresis.

To confirm the switching mechanism of the ubiquitin-barnase fusion protein, and to characterized its structure, stability, and enzymatic function, experiments were performed by the inventors herein upon the purified ubiquitin-barnase fusion protein, obtained as described hereinabove.

Figure 3:
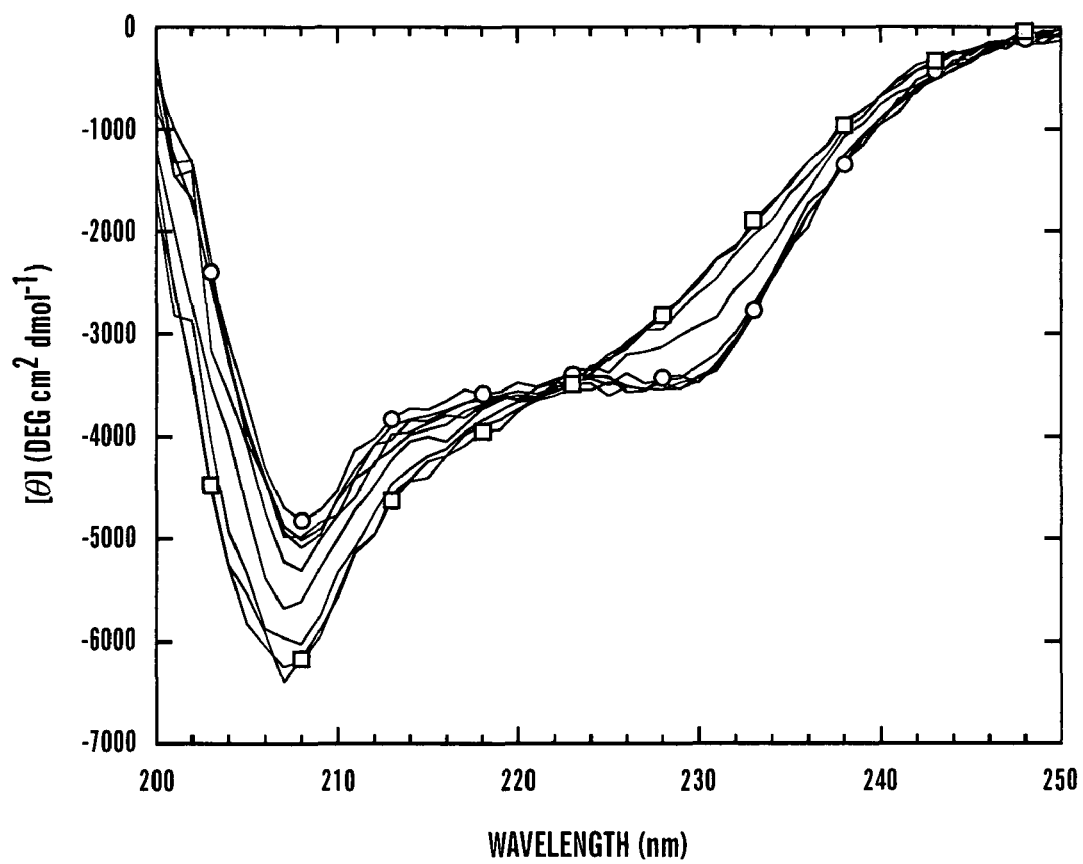
FIG. 3 is a graph of circular dichroism spectra of a ubiquitin-barnase fusion protein as a function of temperature, showing temperature-induced conformational change in the structure of ubiquitin-barnase fusion protein.

All experiments were performed in 10 mM potassium phosphate (pH 7.5), 0.1 M NaCl. The circular dichroism ("CD") spectra as shown in FIG. 3 as a function of temperature. In FIG. 3, circles and squares indicate 5° C. and 50° C., respectively; other scans were recorded at 5° C. increments between these two limits. Below 20° C., the barnase-ubiquitin fusion protein exhibits molar ellipticities and spectral features nearly identical to those of barnase. A particularly diagnostic characteristic of barnase that is also observed for the barnase-ubiquitin fusion protein is a minimum at 231 nM attributed to Trp94. As temperature is increased, however, the spectrum shifts to one that strongly resembles ubiquitin. The 231 nm minimum disappears, and the position and molar ellipticity of the new minimum are consistent with native ubiquitin.

Figure 4:
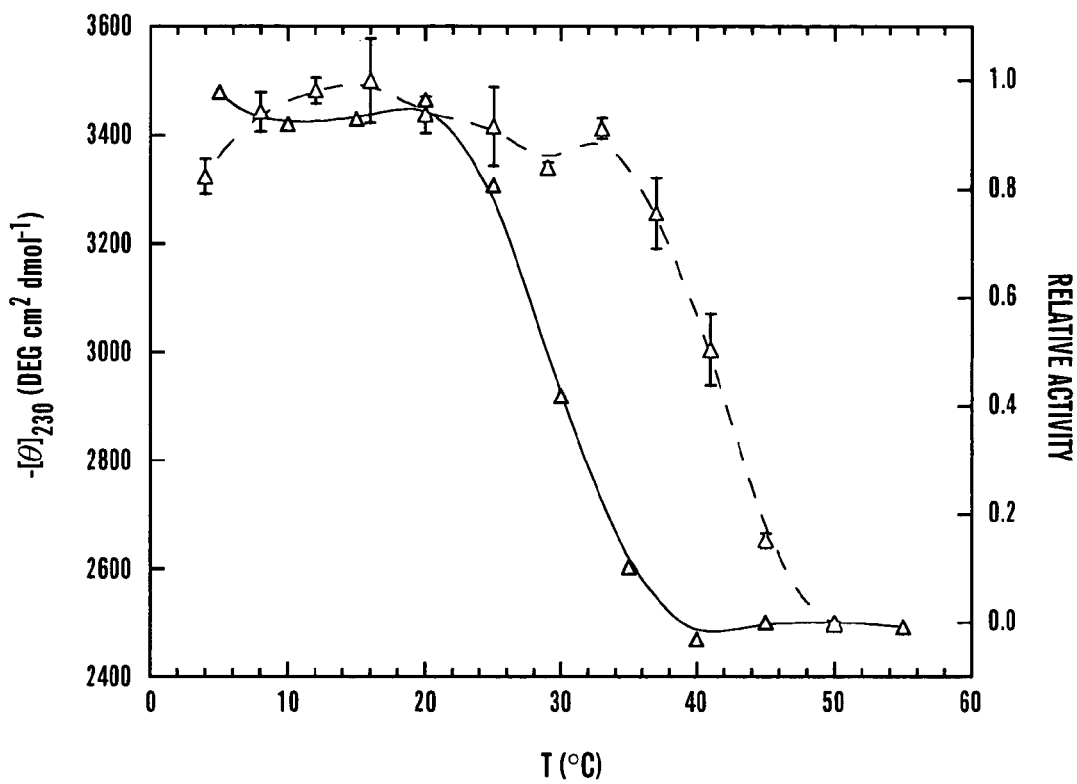
FIG. 4 is graph of the conversion an ubiquitin-barnase fusion protein from the barnase conformation to the ubiquitin conformation, monitored by ellipticity at 230 nm (open triangles, solid line) and barnase enzymatic activity (closed triangles, dashed line). Lines are for illustrative purpose only.

FIG. 4 shows a graph of the conversion of ubiquitin-barnase fusion protein from the barnase conformation to the ubiquitin conformation, monitored by ellipticity at 230 nm (open triangles, solid line) and barnase enzymatic activity (closed triangles, dashed line). Lines are for illustrative purpose only. Activities were determined by recording initial velocities in triplicate (2 mM ubiquitin-barnase fusion protein, 50 mM guanylyl(3 ~5)uridine 3 -monophosphate ("GpUp")) and are normalized to the largest value. As can be seen from FIG. 4, the transition is fully reversible and has a midpoint of about 30 degrees C. Further, it appears to be two-state; an isodichroic point near 223 nm is apparent, and plotting the transition at different wavelengths yields identical midpoints.

The temperature-induced transition from barnase to ubiquitin is consistent with the higher thermal stability of ubiquitin. Ubiquitin and barnase unfold with midpoints of about 100 degrees C. (pH 7) and 55 degrees C. (pH 6.3) respectively. The possibility that the ubiquitin and barnase domains are simultaneously folded is ruled out by the observation that the molar ellipticity of the ubiquitin-barnase fusion protein never exceeds that of the individual proteins at any wavelength or temperature.

Figure 5:
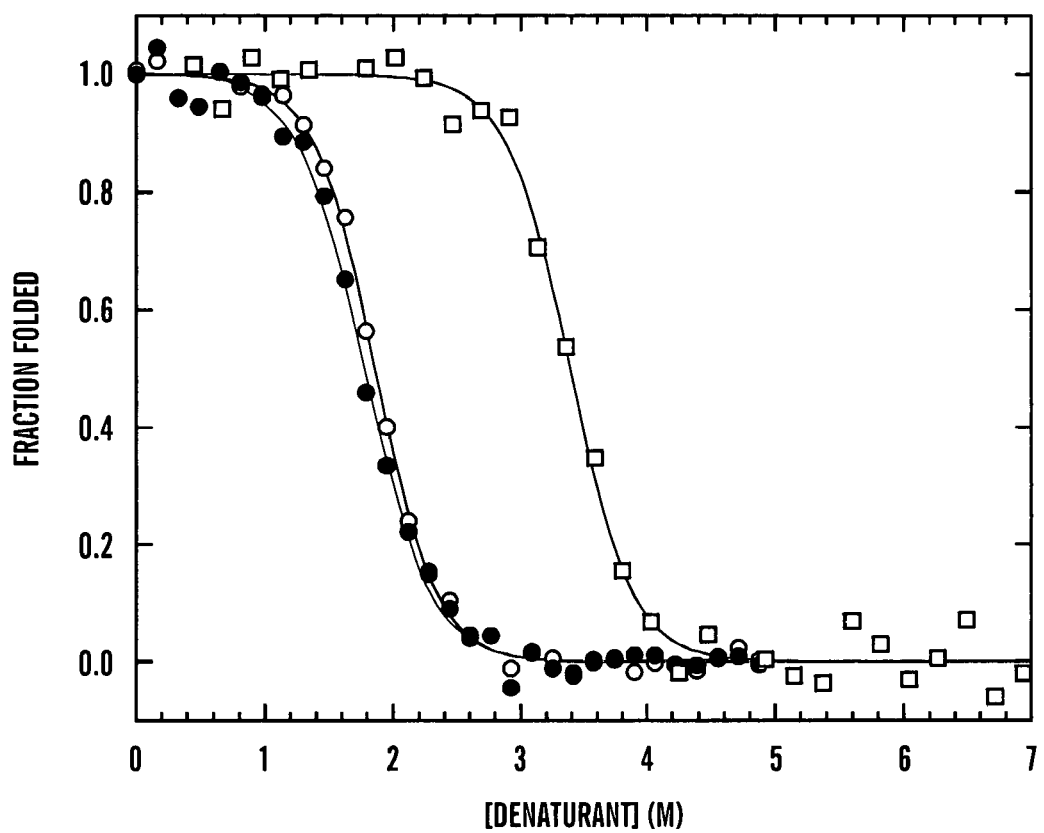
FIG. 5 is a graph showing the denaturation of the barnase domain (10° C., circles) and the ubiquitin domain (40° C., squares) induced by urea and guanidine hydrochloride ("GdnHCl"), respectively.

To further test the mutual exclusivity of ubiquitin and barnase domain folding, the inventors herein monitored urea-induced denaturation by Circular dichroism and Trp fluorescence. Ubiquitin and barnase contain zero and three Trp residues, respectively. Fluoescence is therefore expected to report primarily on structural changes within the barnase domain, whereas Circular dichroism reports on both domains. FIG. 5 is a graph showing the denaturation of the barnase domain (10 degrees C., circles) and the ubiquitin domain (40 degrees C., squares) induced by urea and guanidine hydrochloride ("GdnHCl"), respectively. Data were collected by Circular dichroism at 230 nm (open symbols, black lines) or by Trp fluorescence at 320 nm (closed symbols, grey line). Lines represent best fits to the linear extrapolation equation. At 10 degrees C., the Circular dichroism and fluorescence curves reveal a single cooperative unfolding transition.

It appears to be two-state; thermodynamic parameters obtained by fitting both data sets to the linear extrapolation equation are identical within error (DG=4.1±0.2 kcal×mol−1, m=2.2±0.1 kcal×mol−1×M−1, Cm=2.3±0.05 M). The fact that only one transition is apparent by Circular dichroism confirms that only one domain is folded. The agreement between Circular dichroism and fluorescence curves indicates that this domain is barnase.

If the situation is reversed by raising temperature above 30 degrees C., addition of denaturant at 40 degree C. is predicted to generate an unfolding transition by Circular dichroism but not transition by fluorescence. 6 M urea failed to produce a change in either spectrum. Addition of the stronger denaturant guanidine hydrochloride, however, yields the expected Circular dichroism unfolding transition with the following thermodynamic parameters: DG=8.5±0.1 kcal×mol−1, m=2.5±kcal×mol−1×M−1, Cm=3.4±0.05 M, as shown in FIG. 5.

In contrast to molar ellipticity, fluorescence emission at 320 nm does not change significantly as a function of guanidine hydrochloride concentration, suggesting that the barnase Trp residues are solvent exposed at all denaturant concentrations. This conclusion is supported by the finding that the wavelength of maximum emission remains constant at 356 nm, the value for the unfold barnase. At 10 degrees C., this wavelength shifts from 340 nm in the absence of denaturant to 356 nm in 6 M urea. These data prove that:
 a) folding of the barnase domain includes unfolding of the Ubiquitin domain, and vice versa; and
 b) temperature provides an efficient switch between the two folded conformations of the ubiquitin-barnase fusion protein.

To determine how tightly folding of the ubiquitin domain is coupled to unfolding of the barnase domain, the inventors herein measured the enzymatic activity of the ubiquitin-barnase fusion protein as a function of temperature, using the substrate guanylyl(3'-5')uridine 3'-monophosphate. As shown in FIG. 4, loss of The barnase-ubiquitin fusion protein activity in the ubiquitin-barnase fusion protein mirrors the structural conversion from barnase to ubiquitin, although the apparent midpoint of the former transition occurs at a higher temperature.

A likely reason is that substrate binding in the enzyme assays preferentially stabilizes the barnase domain. The complete loss of barnase activity above 50 degrees C., together with the molar ellipticity values shown in FIG. 3, providing strong evidence that ubiquitin domain folding induces complete unfolding of the barnase domain.

The preceding experimental results suggested to the inventors herein that temperature can be used to regulate cytotoxicity of the ubiquitin-barnase fusion protein in vivo. The inventors herein tested this prediction by transforming E. coli with a plasmid containing the ubiquitin-barnase fusion protein gene and under control of an isopropyl b-D-thiogalacto-pyranoside ("IPTG")-induced T7 promoter. Like barnase, the ubiquitin-barnase fusion protein is extremely lethal. The plasmid was found to be unstable in all strains of E. coli, including those that do not harbor the T7 RNA polymerase gene. Very few transformants were consistently recovered, and in each case the ubiquitin-barnase fusion protein gene was found to contain frameshift or nonsense mutations in the barnase coding region.

To overcome this problem, the inventors herein inserted the barstar gene and its natural promoter from *Bacillus amyloliquefaciens* into the foregoing plasmid, thereby creating a pETMT plasmid that is stable E. coli.

As shown in Table 1 herein below, wherein figures are the averages with standard deviations are obtained from five plates, far fewer colonies were obtained when plates were grown at 15 degrees C. compared to 37 degrees C. Moreover, 36 mg/m L IPTG was sufficient to kill nearly all of the bacteria at 15 degrees C., whereas 143 mg/mL IPTG was required to achieve a comparable result at 37 degrees C.

TABLE 1

Cytotoxicity of the barnase-ubiquitin fusion protein as a function of temperature and isopropyl-β-thiogalactopyranoside concentration
Number of colonies at indicated concentration of IPTG

| T (° C.) | 0 mg/mL | 9 mg/mL | 18 mg/mL | 36 mg/mL | 72 mg/mL | 143 mg/mL |
|---|---|---|---|---|---|---|
| 15 | 14 ± 5 | 35 ± 18 | 39 ± 4 | 0.3 ± 0.5 | 0 ± 0 | 0 ± 0 |
| 37 | 160 ± 40 | 250 ± 60 | 257 ± 40 | 274 ± 30 | 12 ± 4 | 0.60 ± 1 |

These findings reflect the temperature-induced conformational shift from the barnase-form of the ubiquitin-barnase fusion protein to the ubiquitin form. Further, they demonstrate that the ubiquitin-barnase fusion protein/*E. coli* system is highly responsive to the relative stabilities of the two domains within the temperature range of bacterial growth.

Figure 6:
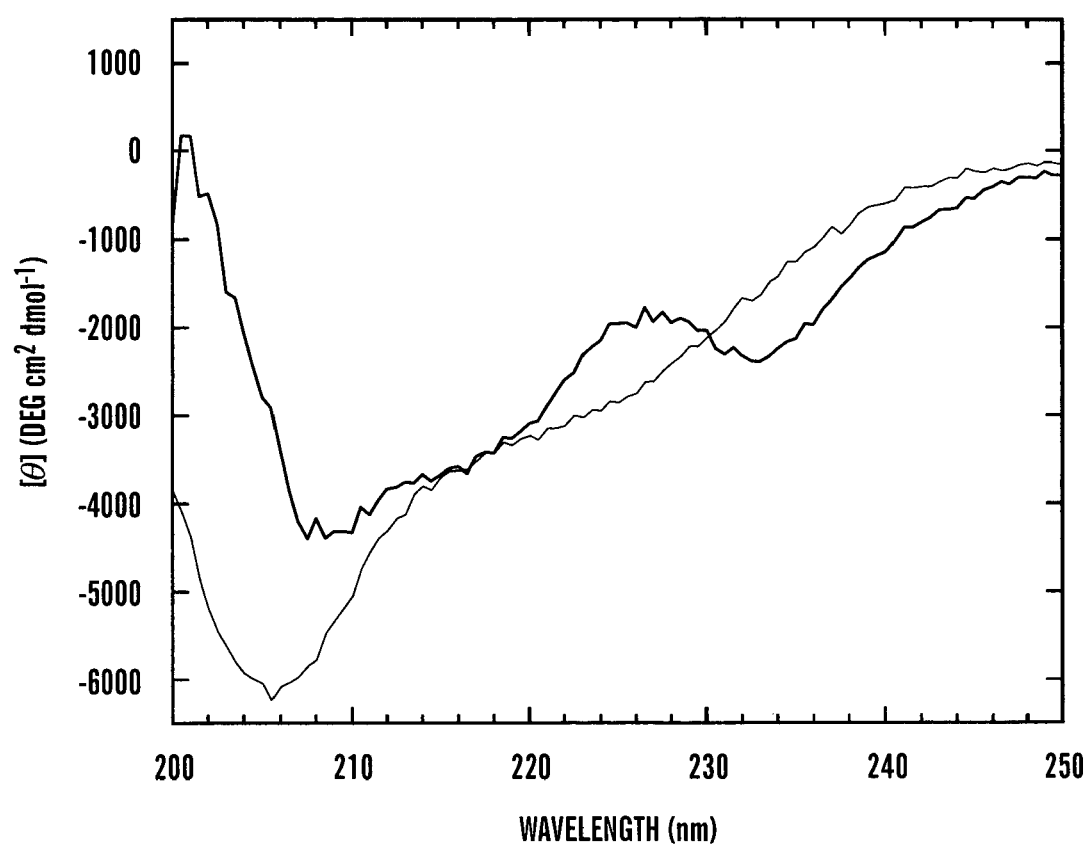
FIG. 6 is a graph of a circular dichroism spectral recording at 40 degrees C., showing barstar-induced folding of the barnase domain and unfolding of the ubiquitin domain.

"Natively-unfolded" proteins contain subunits that are unstructured or partially structured in physiological conditions. The free energy of folding is provided by ligand binding interactions, and the resulting conformational change is used to modulate function of distant domains. The ubiquitin-barnase fusion protein captures this property as well. When barstar is added to the ubiquitin to form of ubiquitin-barnase fusion protein at 40 degrees C., a conformational change is observed. FIG. 6 is a graph of a circular dichroism spectral recording at 40 degrees C., showing barstar-induced folding of the barnase domain and unfolding of the ubiquitin domain. Dotted lines represent 10 mM The barnase-ubiquitin fusion protein in the absence and presence of 12.5 mM barstar, respectively. Black lines were generated by subtracting the circular dichroism spectra of free barstar.

Figure 7:
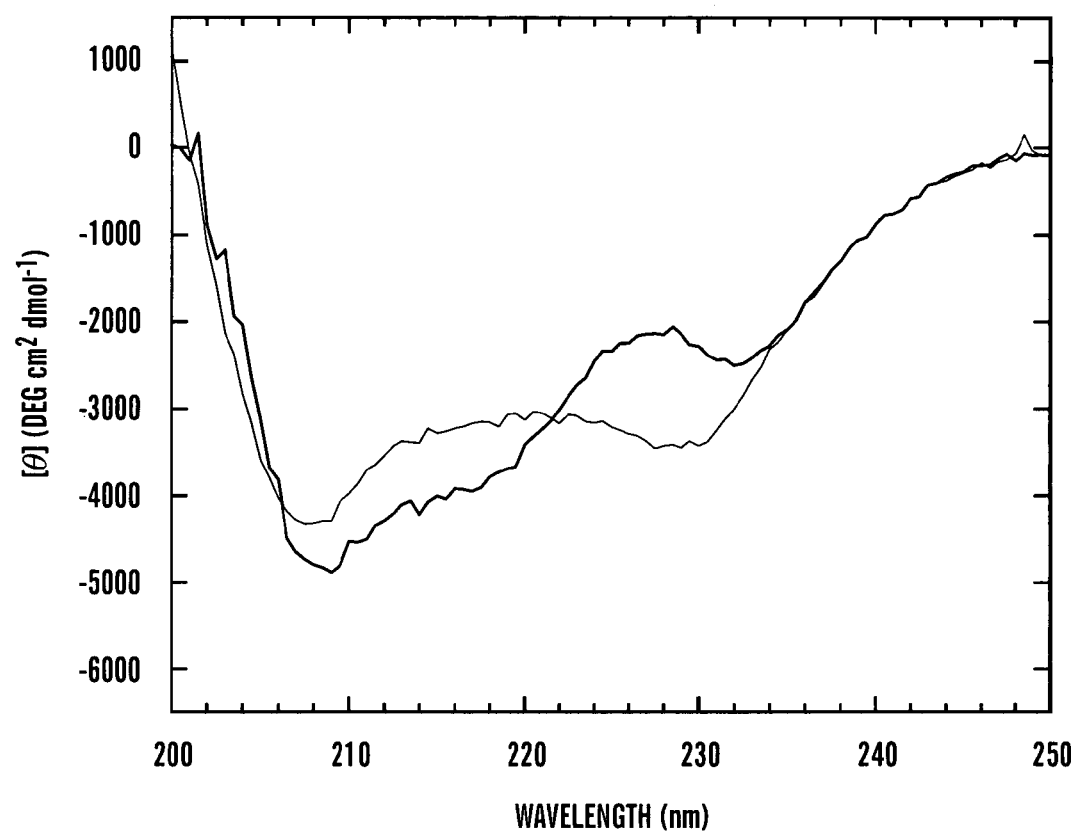
FIG. 7 is a graph of a circular dichroism spectral recording at 15 degrees C., showing barstar-induced folding of the barnase domain and unfolding of the ubiquitin domain.

The circular dichroism spectrum of the ubiquitin-barnase fusion protein-barstar complex, after subtracting the spectrum of free barstar, resembles that of the ubiquitin-barnase fusion protein at 15 degrees C. FIG. 7 is a graph of a circular dichroism spectral recording at 15 degrees C., showing barstar-induced folding of the barnase domain and unfolding of the ubiquitin domain. Dotted lines represent 10 mM The barnase-ubiquitin fusion protein in the absence and presence of 12.5 mM barstar, respectively. Black lines were generated by subtracting the circular dichroism spectra of free barstar. The two are not identical, apparently because of minor structural differences between the free and bound states of barnase and/or barstar. However, Circular dichroism spectra of the ubiquitin-barnase fusion protein-barstar complexes at 40° C. and 15° C. are virtually indistinguishable. This result signifies that ubiquitin domain.

Accordingly, the inventors herein have demonstrated that the folding free energy of one protein domain can be used to drive unfolding of another. Because folding is reversible and inherently cooperative, this mechanism constitutes an efficient and responsive model for a mutually exclusive domain folding molecular switch for, inter alia, coupling conformational change to protein function. The cytotoxic activity of barnase in the present invention provides the basis for several novel applications. For example, stability-enhanced ubiquitin variants can be rapidly identified from combinatorial libraries by their ability to allow *E. coli* to survive at temperatures less than 30 degrees C. in the presence of 36 mg/mL IPTG A major advantage that this fusion protein affords over other directed evolution techniques, such as, for example, phage display, is that the entire selection takes place inside a living bacterium, and stabilizing mutations are sorted from destabilizing mutations in the most efficient and decisive manner possible. This fusion protein is general and can be applied to other proteins, including those too large to be expressed on the phage surface. If necessary, known stabilizing or destabilizing mutations can be introduced into the barnase domain in order to make the target protein optimally responsive to the inserted protein. Additionally, the fusion protein can be modified to generate a class of cytotoxic molecules with novel sensor capabilities. For example, the fusion protein allows ribonuclease activity to be turned on and off by ligand binding to an engineered regulatory domain. Ligand binding domains from any one of a large number of proteins can perform this function as long as they meet the structural design novel described hereinabove. This invention forms the basis for developing cytotoxic proteins that are activated by a wide variety of cell-specific effector molecules, and can thus target cancerous or virtually infected cells for destruction.

We claim:

1. A fusion protein comprising a ubiquitin insert protein having an insert regulatory domain lying between an amino terminal and a carboxyl terminal of the ubiquitin insert protein; and, a barnase target protein having a surface loop that begins at an alpha carbon of an initial terminal amino acid of the surface loop and terminates at an alpha carbon of a terminal amino acid of the surface loop, the surface loop comprising a cytotoxic target domain of the barnase target protein, wherein, the ubiquitin insert protein is inserted at a point within the surface loop between the alpha carbon of the initial amino acid of the surface loop and the alpha carbon of the terminal amino acid of the surface loop, such that an amino-carboxyl length of the ubiquitin insert protein is at least two-times greater than an alpha-carbon-alpha-carbon length of the surface loop of the barnase target protein wherein the insert regulatory domain exists in either a folded or unfolded conformation and the target cytotoxic domain exists in either a folded or unfolded conformation, the insert regulatory domain and the target cytotoxic domain comprising a cooperative and reversible conformational equilibrium such that if the insert regulatory domain is in its folded conformation, the target cytotoxic domain is in its unfolded conformation and vice versa.

2. The fusion protein of claim 1, wherein the target cytotoxic domain folds under the influence of a first controllable effector signal, and the insert regulatory domain folds under the influence of a second controllable effector signal.

3. The fusion protein of claim 1, wherein the first controllable effector signal is selected from the group comprising ligand binding, pH, and temperature in either the insert domain or the target domain.

4. The fusion protein of claim 1, wherein the second controllable effector signal is selected from the group comprising ligand binding, pH, and temperature in either the insert domain or the target domain.

5. The fusion protein of claim 1, wherein the insert protein comprises human ubiquitin, the insert regulatory domain comprises a regulatory domain of human ubiquitin, the target protein comprises barnase, the target cytotoxic domain comprises a cytotoxic domain of barnase, the amino-carboxyl length is about 38 Å, the initial amino acid of the surface loop comprises proline in the number 64 positions ("Pro64"), the terminal amino acid of the surface loop comprises threonine in the number 70 position ("Thr70"), and the alpha-carbon-alpha-carbon length is about 10.4 Å, and wherein the insert protein is inserted between amino acid residue 66 and amino acid residue 67 of the target protein.

6. The fusion protein of claim 5, wherein the regulatory domain of human ubiquitin and the cytotoxic domain of barnase comprise either a folded or unfolded conformation which folded or unfolded conformation is subject to the influence of controllable first and second effector signals.

7. A method of making the fusion protein of claim 1, comprising: selecting a linker containing first and second restriction sites between a Lys66 and a Ser67 codon of a barnase gene; using said first and second restriction sites of said linker to operationally insert a ubiquitin gene between two amino-acid codons of said linker, thereby creating a ubiquitin-barnase fusion gene; fully sequencing said ubiquitin-barnase fusion gene to verify its integrity; using enzymes to operationality insert said ubiquitin-barnase fusion gene into any plasmid of a BL21 (De3) family, thereby creating an interim ubiquitin-barnase fusion expression plasmid; operationally inserting a gene for barstar and its normal promoter from *Bacillus amyloliquefaciens* into said interim ubiquitin-barnase fusion expression plasmid, thereby creating a ubiquitin-barnase fusion-barstar complex plasmid; cloning said gene for barstar into a T7 promoter-containing plasmid conferring resistance to an antibiotic other than ampicillin onto cells transformed by said T7 promoter-containing plasmid, thereby creating a barstar plasmid; transforming *E. coli* BL21 (De3) cells grown at about 29 to 37 degrees C. in any medium compatible with *E. coli* growth using both said barstar plasmid and said ubiquitin-barnase fusion-barstar complex plasmid, and inducing said *E. coli* BL21 (DE3) cells with about 100 mg/L isopropyl b-D-thiogalactopyranoside; harvesting said transformed *E. coli* cells by centrifugation after about 2 to 12 hours after said induction; placing said harvested *E. coli* cells in 10 mM sodium phosphate at a pH of 7.5, thereby creating a solution of harvested *E. coli* cells; lysing said solution of harvested *E. coli* cells by repeated freeze-thaw cycles in the presences of about 10 mg/liter lysozyme, thereby creating a lysate; adding about 10 mg/liter DNase I to reduce the viscosity of said lysate; centrifuging said reduced viscosity lysate to remove insolubles, thereby forming a supernatant; adding about 8 M urea to said supernatant to dissociate bound barstar; removing said dissociated barstar from said supernatant by passing said supernatant through an anion exchange chromatography resin to yield a solution; loading said solution onto a cation exchange column; washing said solution with about 10 mM sodium phosphate (pH about 7.5) and about 6 M urea; eluting said solution using a 0 to 0.2 M NaCl gradient; and removing said urea from said dilution by dialysis against double-distilled water to yield ubiquitin-barnase fusion protein.

* * * * *

UNITED STATES PATENT AND TRADEMARK OFFICE
CERTIFICATE OF CORRECTION

| | | |
|---|---|---|
| PATENT NO. | : 7,767,788 B2 | Page 1 of 1 |
| APPLICATION NO. | : 10/802516 | |
| DATED | : August 3, 2010 | |
| INVENTOR(S) | : Stewart Loh et al. | |

It is certified that error appears in the above-identified patent and that said Letters Patent is hereby corrected as shown below:

Claim 7, col. 14, line 36, please delete "29" and insert --20--.

Signed and Sealed this
Twenty-fifth Day of January, 2011

David J. Kappos
*Director of the United States Patent and Trademark Office*